(12) United States Patent
Kramer et al.

(10) Patent No.: US 8,778,370 B2
(45) Date of Patent: Jul. 15, 2014

(54) METHOD AND COMPOSITION FOR INHIBITING GROWTH OF MICROORGANISMS IN INDUSTRIAL PROCESS WATERS IN THE PRESENCE OF ANIONIC ANTI-FOULING ADDITIVES

(75) Inventors: Shira Kramer, Timonium, MD (US); Jeffrey Berresford, Seven Fields, PA (US); Mark Wozniak, Bel Air, MD (US); Alexander M. Josowitz, Baltimore, MD (US)

(73) Assignee: Sterilex Corporation, Hunt Valley, MD (US)

( * ) Notice: Subject to any disclaimer, the term of this patent is extended or adjusted under 35 U.S.C. 154(b) by 729 days.

(21) Appl. No.: 12/689,946

(22) Filed: Jan. 19, 2010

(65) Prior Publication Data

US 2010/0183738 A1    Jul. 22, 2010

Related U.S. Application Data

(60) Provisional application No. 61/194,000, filed on Jan. 16, 2009.

(51) Int. Cl.

| | | |
|---|---|---|
| *A01N 25/00* | (2006.01) | |
| *A01N 59/26* | (2006.01) | |
| *A61K 33/42* | (2006.01) | |
| *A61K 33/40* | (2006.01) | |
| *A01N 59/02* | (2006.01) | |
| *A61K 33/04* | (2006.01) | |
| *C02F 1/72* | (2006.01) | |
| *C02F 1/50* | (2006.01) | |
| *A01N 37/16* | (2006.01) | |
| *A01N 59/00* | (2006.01) | |
| *C02F 1/66* | (2006.01) | |
| *C02F 103/02* | (2006.01) | |

(52) U.S. Cl.
CPC .............. *A01N 37/16* (2013.01); *C02F 1/722* (2013.01); *C02F 2303/20* (2013.01); *C02F 2303/04* (2013.01); *C02F 1/50* (2013.01); *C02F 1/66* (2013.01); *C02F 2305/04* (2013.01); *C02F 2209/06* (2013.01); *A01N 59/00* (2013.01); *C02F 2103/023* (2013.01); *C02F 2303/08* (2013.01)
USPC ............ 424/405; 424/601; 424/616; 424/705

(58) Field of Classification Search
USPC ......................................... 424/616
See application file for complete search history.

(56) References Cited

U.S. PATENT DOCUMENTS

| | | | | |
|---|---|---|---|---|
| 4,719,083 | A | * | 1/1988 | Baker et al. ..................... 422/15 |
| 5,320,805 | A | * | 6/1994 | Kramer et al. .................. 422/28 |
| 5,382,367 | A | * | 1/1995 | Zinkan et al. ................. 210/698 |
| 6,372,771 | B1 | * | 4/2002 | Ludwig et al. ................ 514/383 |
| 6,784,168 | B1 | * | 8/2004 | Jones et al. ..................... 514/76 |
| 2007/0181510 | A1 | * | 8/2007 | Harvey et al. ................. 210/759 |
| 2010/0298275 | A1 | * | 11/2010 | Yin et al. ....................... 514/129 |

FOREIGN PATENT DOCUMENTS

JP           10277560 A  * 10/1998

OTHER PUBLICATIONS

Nishimura, et al. JP 10-277560A, Internet Translation, 1998, pp. 1-9.*
Amjad et al., *The Effect of Biocides on Deposit Control Polymer Performance*, Association of Water Technologies, The Lubrizol Corporation, 2007.
Frayne, *Cooling Water Treatment, Principles and Practice*, Chemical Publishing Company, 1999, p. 220.

* cited by examiner

*Primary Examiner* — Alton Pryor
(74) *Attorney, Agent, or Firm* — Michael David, Esq.; Capitol City TechLaw, PLLC

(57) ABSTRACT

A composition and method for treating industrial water is described, wherein the composition has microbe inhibiting properties. The composition utilizes a cationic phase transfer agent, such as a quaternary ammonium compound in the presence of a peroxide source. The composition does not significantly reduce the anti-scaling properties of anionic dispersants present in the water.

20 Claims, No Drawings

METHOD AND COMPOSITION FOR INHIBITING GROWTH OF MICROORGANISMS IN INDUSTRIAL PROCESS WATERS IN THE PRESENCE OF ANIONIC ANTI-FOULING ADDITIVES

This application claims priority from U.S. Provisional Application No. 61/194,000, filed Jan. 16, 2009.

BACKGROUND OF THE INVENTION

1. Field of the Invention

The present invention generally relates to the field of industrial water treatment using cationic phase transfer agents in the presence of anionic anti-corrosive and anti-scaling agents.

2. Background of the Prior Art

Microorganisms are found in open and closed water cooling systems found in industrial and commercial settings. The presence of microorganisms within these waters can lead to the formation of biological deposits on process machinery and lead to problems of corrosion, heat transfer problems, pump blockages and breaking, dissemination of pathogenic microorganisms to humans and animals (e.g. *Legionella*), and many other problems. To control microbial growth, biocides, biostats, and biodispersants are added to the water. Currently available biocides include oxidizing and non-oxidizing biocides like chlorine, ozone, chlorine dioxide, stabilized bromine, glutaraldehyde, quaternary ammonium compounds and others.

Deposit accumulations resulting from the precipitation of calcium salts is an additional problem in modern open water cooling systems. The precipitation of calcium salts can lead to corrosion and formation of scale deposits in industrial and commercial water systems. The formation of the scale deposits results in decreases in the heat transfer efficiency and the carrying capacity of water distribution systems. Chemicals are often added to the process water systems to control corrosion and scaling of these water systems. Anionic anti-corrosion and anti-scaling agents based upon acrylates, polyacrylates, acrylic acid terpolymers, acrylamido methyl propyl sulfonic acid (AMPSA), and PBTC (2-phosphonobutane-1,2,4-tricarboxylic acid) are effective at preventing corrosion and scaling of open and closed water cooling systems.

Unfortunately the anionic agents used to control water born and water formed deposits are also incompatible with cationic surfactants, including quaternary ammonium compounds in solution. The cationic surfactant compounds, in effect, may perhaps bind to the anionic agents preventing them from acting as anti-scale and anti-corrosive additives. As a result, the highly biologically effective and broad class of chemicals known as quaternary ammonium compounds are not generally used in commercial and industrial water cooling systems that also utilize anionic anti-corrosion and anti-scaling agents.

SUMMARY OF THE INVENTION

In one aspect, the invention provides a method for treating microbial growth in an industrial water system. The water body of the system contains an anionic anti-scale or anti-corrosive agent. In accordance to the invention, a composition is added to the body of water in an industrial water system which comprises anti-scaling/anti-corrosive agents. The composition comprises a peroxide source and a positively charged phase transfer agent. Optionally, the method includes adding an alkaline compound. The water treatment process, before addition of the alkaline compound is at a pH value of 7.0 or higher or is brought to that pH value by the addition of the alkaline compound. The anti-scaling agent retains anti-scaling effectiveness, and the composition has antimicrobial or biocidal activity.

In accordance to one embodiment, the peroxide source comprises a per salt, a hydrogen peroxide, or an organic peroxide. In a preferred embodiment, the peroxide is at about 50 ppb and 10,000 ppm within the body of water.

In accordance to another embodiment, the positively charged phase transfer agent is at least one from among phosphonium salt, iodide, sulfonium salt, and a quaternary ammonium salt. Preferably, the positively charged phase transfer agent is at least one quaternary ammonium compound. At use, preferably the positively charged phase transfer agent is at about 50 ppb and 10,000 ppm within the body of water. In accordance to one embodiment, the quaternary ammonium compound is an alkyl dimethyl benzyl ammonium chloride, an alkyl dimethyl ethylbenzyl ammonium chloride, a dialkyl dimethyl quaternary compound, or a mixture thereof.

In accordance to one embodiment, the anionic anti-scaling and anti-corrosive agent is at least one from among acrylates, polyacrylates, acrylic acid terpolymers, acrylamido methyl propyl sulfonic acid, and (2-phosphonobutane-1,2,4-tricarboxylic acid).

In accordance to another embodiment, the composition either includes the alkaline compound or the alkaline compound is added to the body of water separately of the composition, either at the time of the addition of the composition or before the addition of the composition.

In accordance to yet another embodiment, the composition further includes at least one from among a surfactant, a dye, a gelling agent and a peroxide activator.

In accordance to still another embodiment, the composition is prepared as a mixture, or is prepared and transported to the site of end-use as separate compounds or partial mixtures of the compounds therein. In accordance to one embodiment, the mixtures or compounds of the composition are prepared and transported to the site of end-use as powder(s), liquid(s), pellets or tablet(s), or combinations of these forms. In accordance to yet another embodiment, the composition or compounds thereof are diluted in solvent to prepare concentrated solutions of the composition or the compounds thereof, prior to their addition to the body of water in the industrial water system.

In accordance to still yet another embodiment, the composition when in concentrated form comprises peroxide is at a concentration of between about 0.5% and about 90%, preferably at a concentration of between about 1% and about 50% in the concentrated solution.

In accordance to still yet another embodiment, the composition when in concentrated form comprises the quaternary ammonium compound at a concentration of between about 0.5% and about 90%.

At use, the concentration of the quaternary ammonium compound is between about 50 ppb and about 100,000 ppm, preferably between about 50 ppb and about 100,000 ppm; the concentration of the peroxide is between about 3 ppm and about 10,000 ppm.

In accordance to another aspect, the invention provides a composition compatible with use in a water treatment process which comprises use of anionic dispersants, said composition comprising:
 a peroxide source,
 a positively charged phase transfer agent, and
 optionally, an alkaline compound, wherein the water treatment process before addition of the alkaline compound is at a pH of between greater than 7.0 or is brought to that pH value by the addition of the alkaline compound, wherein said composition is used in a water treatment process in the presence of dispersant agents which remain effective at preventing scaling, and wherein the composition inhibits the growth of microorganisms within the industrial water.

DETAILED DESCRIPTION OF THE INVENTION

Pursuant to the present invention, it has been unexpectedly discovered that a composition comprising a peroxide and a positively-charged quaternary ammonium compound (QAC) can be used as a microbiocide and anti-biofilm agent in open and closed loop water cooling systems at a pH greater than about 7 concomitantly with the use of anionic dispersants and compounds to control corrosion and scaling, without binding or precipitation of the anionic anti-scaling and anti-corrosion agents out of solution or in some other manner rendering the anionic dispersants ineffective. Without limiting the invention to any mechanism of action, it is believed that under the right conditions (e.g. pH equal or greater than about 7.0, more preferably greater or equal to about 8.0), the proton from the hydrogen peroxide is extracted leaving a negatively charged hydroperoxide ion (OOH—). The hydroperoxide ion then becomes associated with the quaternary ammonium ion. The resultant amphiphilic quaternary ammonium hydroperoxide pair in effect limits or decreases the ability of the cationic quaternary ammonium component to interact with the anionic anti-scaling or anti-corrosive additive. It has also been demonstrated that the resultant amphiphilic quaternary ammonium hydroperoxide pair has enhanced biocidal and biofilm removal properties in part due to its enhanced solubility in both aqueous and in the lipid phases of biofilms and microorganisms.

Any peroxide may be part of the composition of the invention. Examples of peroxide types useful in the invention include per-salts (i.e. peroxide salts), hydrogen peroxide, or organic peroxides (e.g. benzoyl peroxide, etc.).

The per-salts used in this invention are alkaline salts having hydrogen peroxide of crystallization or form peroxide upon dissociation. When the per-salts are dissolved in a suitable solvent, preferably a water based solvent, a peroxide ion is released. Examples of suitable per-salts include percarbonates, perborates, persilicates and perphosphates. A preferred per-salt is sodium percarbonate (i.e. a carbonate perhydrate).

A preferred embodiment of this invention uses a quaternary ammonium compound as a phase transfer agent having biocidal or antimicrobial properties. However, other positively charged phase transfer agents can be used. A "phase transfer agent" is an agent that transfers one or more reagents (e.g. a hydroperoxide ion) to a location where it can conveniently react with another agent (e.g. an organic biofilm structure or cell membrane). The phase transfer agents embodied by this invention include cationic surfactants and polymeric cationic surfactants. The positively charged phase-transfer agent of the invention include a phosphonium salt such as t-butyl phosphonium, iodide, sulfonium salt such as tributyl sulfonium chloride, or a quaternary ammonium salt.

Quaternary ammonium compounds ("QACs") generally have the following formula $R_1R_2R_3R_4N^+X^-$. Depending on the nature of the R groups, the anion, and the number of quaternary nitrogen atoms present, the antimicrobial QAC are typically classified as mono alkyl trimethyl ammonium compounds, mono alkyl dimethyl benzyl ammonium salts, dialkyl dimethyl ammonium salts, heteroaromatic ammonium salts, polysubstituted quaternary ammonium salts, bisquaternary ammonium salts or polymeric ammonium salts. Examples of mono alkyl trimethyl ammonium salts include cetyl trimethyl ammonium bromide (CTAB); alkyl trimethyl ammonium chloride; alkyl aryl trimethyl ammonium chloride; cetyl dimethyl ethyl ammonium bromide. Examples of mono alkyl dimethyl benzyl ammonium salts include alkyl dimethyl benzyl ammonium chlorides; dodecyl dimethyl 3,4 dichlorobenzyl ammonium chloride; and mixtures of alkyl dimethyl benzyl and alkyl dimethyl substituted benzyl(ethyl benzyl) ammonium chlorides. Examples of dialkyl dimethyl ammonium salts include didecyl dimethyl ammonium halides and octyl dodoceyl dimethyl ammonium chlorides. Examples of heteroaromatic ammonium salts include cetylpyridinium halide (CPC); 1-[3-chloroallyl]-3,5,7-triaza-1-azoniaadamantane; alkyl-isoquinoliniumm bromide and alkyldimethylnaphthylmethyl ammonium chloride. Examples of poly-substituted quaternary ammonium compounds include alkyl dimethyl benzyl ammonium saccharinate and alkyl dimethylethylbenzyl ammonium cycloheylsulfamate. Examples of bis-quaternary ammonium salts include 1,10-bis(2-mthyl-4-aminoquinolinium chloride)-decane; b1,6-Bis[1-methyl-3-(2,2,6-trmethyl cyclohexyl)-propyldimethyl ammonium chloride]hexane. All these QACs have antibiotic activity and are phase transfer agents in accordance with the invention.

Particularly suitable quaternary ammonium compounds for the invention are alkyl dimethyl benzyl ammonium chlorides, alkyl dimethyl ethyl benzyl ammonium chlorides, dialkyl dimethyl quaternary compounds or mixtures of these quaternary compounds.

Alkyl dimethyl benzyl ammonium chlorides preferably used have an alkyl group which is a mixture of about 50% C14, 40% C12 and 10% C16. Another alkyl dimethyl benzyl ammonium chloride preferably used has an alkyl group which is a mixture of about 5% C12, 60% C14, 30% C16 and 5% C18.

Alkyl dimethyl ethyl benzyl ammonium chlorides preferably used in the invention include those where the distribution of alkyl groups are about as follows: 50% C12, 30% C14, 17% C16 and 3% C18. Another group of preferred quaternary ammonium compound used in the invention are alkyl dimethyl ethyl benzyl ammonium chlorides where the alkyl group has the distribution of about 68% C12 and about 32% C14.

Dialkyl dimethyl ammonium chlorides preferably used include didecyl dimethyl ammonium chlorides; dioctyl dimethyl ammonium chloride; didecyl dimethyl ammonium chloride and octyl dodecyl dimethyl ammonium chloride.

Mixtures of the quaternary ammonium compounds would also be suitable for the invention.

Optionally, one of a number of different sequestering agents commonly used in industrial processing water systems may be used in the composition. These sequestering agents can be selected from a group consisting of 8-hydroxyquinoline, ethylenediaminetetraacetic acid (EDTA) or its derivatives, 1 hydroxyethylidene-1,1-diphosphonic acid (HEDP) and its derivatives, sodium pyrophosphate, potassium hypophosphite, and sodium tripolyphosphate.

The present invention also provides a method to control the growth of microorganisms by which the composition described above is added to an industrial or commercial water system containing an anionic dispersant or anti-scaling/corrosion agent and having a pH greater than about 7.0, preferably at a pH of about 7.5 or greater, or more preferably at a pH greater than about 8.0.

In another embodiment of the invention, the method may involve the addition of an alkalinity source to the water system to bring the pH of the water system to a pH greater than about 7.0 or more preferably to a pH greater than about 8.0. The pH of the water system should be brought to the preferred pH prior to or at approximately the same time as when the composition described above is added. The pH may be adjusted by the addition of a source of alkalinity to the industrial water system. The pH of the water system may be adjusted by the addition of any number of alkalinity agents, including but not limited to sodium hydroxide, potassium hydroxide, sodium carbonate, potassium carbonate, etc. The pH may also be adjusted by adding ammonia, amines or other organic bases.

Optionally the source of alkalinity might be added directly to the composition containing the peroxide source and phase transfer agent, such that upon addition of the composition to an industrial water processing system, the water in the system reaches a pH greater than about 7.0, or more preferably greater than about 8.0 after the addition of the composition. The alkalinity can be achieved in a number of ways but most likely will involve one or more alkaline metal salts of carbonates, oxides or hydroxides. Suitable examples include sodium hydroxide, potassium hydroxide, sodium carbonate, potassium carbonate, etc. The alkalinity source may also be ammonia, amines or other organic bases.

The composition placed in an industrial water process was shown to retain its biocidal, antimicrobial, and biofilm removal properties. The composition placed in an industrial water process was shown to exhibit significantly less interference with the anti-scaling and anti-corrosion effects of an anionic dispersant present in the solution than would be expected from the same quaternary ammonium compound added without a peroxide source. Examples of anionic anti-scaling and anti-corrosive agents include acrylates, polyacrylates, acrylic acid terpolymers, acrylamido methyl propyl sulfonic acid (AMPSA), and PBTC (2-phosphonobutane-1,2,4-tricarboxylic acid). A limited reduction in the efficacy of the dispersant may occur, with at most 25% of dispersant efficacy lost. In most circumstances, the reduction in dispersant efficacy is less than 20%, and preferably less than 15%, 10%, or 5%, or is about 0%.

The proposed composition is suitable for use in any water system including those where anionic dispersants are used to control corrosion and scaling. The invention allows the use of the solution of the invention "on-line" i.e., concomitantly with the usage of the anionic dispersants and while the industrial water system is in normal use. Such industrial water systems include but are not limited to open recirculating and closed loop cooling water systems, water purification systems, de-ionized water systems, potable water systems, automotive weld water systems, injection molding systems, brewery utility and packaging systems, pasteurizing systems, hospital water systems, dental unit water systems, HVAC systems, ultrafiltration systems, scrubber water systems, air washer systems, steel manufacturing water systems, alkaline papermaking systems, stock chest preservation systems and down-hole drilling systems.

An artisan skilled in the art could easily figure in light of this disclosure various combinations within the scope of the concept described and illustrated herein. For example, it is possible to combine peroxide of different kinds and from different sources, to add sequestering agents and use other/additional cationic phase-transfer agents to similar effect and to use the composition in industrial and commercial water systems containing anionic dispersants or anti-scaling and antifouling agents for which it is desirable to prevent the interaction of the cationic phase-transfer agent with the anionic dispersants.

The composition may also contain a number of additional additives that may be advantageous or may be used to deliver the composition to the site of the intended treatment. These include but are not limited to surfactants, dyes such as fluorescein, gelling agents such as carboxymethyl cellulose, clays, attapulgite and bentonite. In addition the composition may also contain peroxide activators such as enzymes, iodides and hemin.

Surfactants that may be used with this invention include nonionic surfactants, an amphoteric surfactant, other cationic surfactants, or mixtures thereof.

The composition of the invention may be prepared, stored and delivered to a place of end-use in the form of a powder, liquid, pellet, or tablet. Individual components or mixtures of some components may be prepared, if desired, separately and delivered to the site of end use separately or premixed. As appropriate, any ingredients used in the composition may be dissolved in an appropriate solvent, e.g. water, prior to being used to make the composition disclosed.

A wide range of concentrations of peroxide source, positively charged phase transfer agent and sequestering agents are effective. In one embodiment of this invention, the composition is delivered in a concentrated form and added to the water system at the appropriate concentration. The composition may also contain or may have additional ingredients added prior to its use. For example, hydrogen peroxide is typically unstable at an alkaline pH. Therefore, the source of optional alkalinity may be delivered separately from the composition containing the hydrogen peroxide, the two compositions being blended or mixed into a single composition prior to use, or delivered separately to the industrial water body.

The concentrated composition optionally may be diluted with an appropriate solvent prior to use and that, if needed, other ingredients be added prior to treatment. The preferred solvent is water.

In a concentrated form, the peroxide may range in concentration from about 0.5% to 90%, and preferably from about 1% to about 50%. The cationic transfer agent of the composition may be in the range from about 0.5% to about 90%. (These and all other % figures disclosed herein are in consideration of the weight of the chemicals (i.e., w:w), unless clearly contradicted by the context). More preferably, the cationic phase transfer agent of the composition is in the range of about 1% to about 16%.

At use, the amount of peroxide will be in a range from about 50 ppb to about 100,000 ppm. More preferably, the concentration of peroxide will be in the range from about 3 ppm to about 10,000 ppm. At use, the amount of positively charged transfer agent will be in the range from about 50 ppb to about 100,000 ppm. More preferably, the concentration of positively charged transfer agent will be in the range from about 3 ppm to about 10,000 ppm.

Although not meant to limit the scope of this invention, the method used to deliver the composition may involve adding the composition or individual components directly to the process water at a level needed to obtain the desired concentration of peroxide and quaternary ammonium compound needed to control microbial growth, without first preparing concentrated solutions.

In another embodiment, the method used to deliver the composition involves the slow, continuous addition of the composition to the process water. The addition of the composition on a continuous basis can be done in a number of different ways. These include continuous drip systems, metering pumps, powder feeders, controlled dissolution, etc. The examples given should not limit the scope and methods used to deliver the composition on a continuous basis.

The liquids of the composition can be prepared using a low speed mixer in a vessel capable of holding the liquid. The mixtures are stirred until they are homogeneous (typically about 10 minutes). The mixer may be of any number of types suitable in for mixing liquids. The mixer should be constructed of materials appropriate for alkaline and peroxide solutions. The vessel should also be suitable for alkaline as well as peroxide solutions.

Example 1

The concentrated solutions listed below comprise the following ingredients at the indicated concentrations. The two solutions are prepared separately. The mixture may also be diluted with a solvent prior to use, if needed. The preferred solvent is water.

| Component | Wt Percent | Source |
| --- | --- | --- |
| Solution A: | | |
| n-alkyl dimethyl ethylbenzyl ammonium chloride/n-akyldimethylbenzyl ammonium chloride mixture | 6.00% | Barquat 4250Z (Lonza, Inc.) |
| Hydrogen Peroxide | 6.30% | Solvay |
| Water | 87.7% | Deionized |
| Solution B: | | |
| Soda Ash | 6.00% | General Chemical Corp |
| Potassium Carbonate | 6.00% | Armand Products |
| Tetrasodium ethylenediaminetetraacetate | 13.0% | Dow Chemical |
| Water | 75.0% | Deionized |

Prior to use, equal volumes of the Solution A and Solution B are added together, mixed until homogenous, and dosed to provide upon use hydrogen peroxide concentrations between about 50 ppb and 10,000 ppm and quaternary ammonium concentrations to between about 50 ppb and 10,000 ppm.

Example 2

A two-part solution that is intended to be mixed together prior to use is prepared with the following ingredients and concentrations. The mixture may also be diluted with a solvent prior to use, if needed.

| Component | Wt Percent | Source |
| --- | --- | --- |
| Solution A: | | |
| Hydrogen Peroxide | 1.05% | Solvay |
| Water | 98.95% | Deionized |
| Solution B: | | |
| Soda Ash | 1.77% | General Chemical Corp |
| Tetrasodium ethylenediaminetetraacetate | 2.17% | Dow Chemical |
| n-alkyl dimethyl ethylbenzyl ammonium chloride/n-akyldimethylbenzyl ammonium chloride mixture | 1.00% | Lonza |
| FD&C Red #28 | 0.001% | Pylam |
| Water | 95.06% | Deionized |

Prior to use, equal volumes of the Solution A and Solution B are added together, mixed until homogeneous and used as is. It is also possible to dilute the mixture of Solution A and Solution B with an appropriate level of water to decrease the concentration of hydrogen peroxide and quaternary ammonium compounds.

Example 3

A concentrated solution is prepared with the following ingredients and concentrations. The mixture may also be diluted with a solvent prior to use, if needed.

| Component | Wt Percent | Source |
| --- | --- | --- |
| n-alkyl dimethyl ethylbenzyl ammonium chloride/n-akyldimethylbenzyl ammonium chloride mixture | 6.00% | Barquat 4250Z (Lonza, Inc.) |
| Hydrogen Peroxide | 6.30% | Solvay |
| Soda Ash | 6.00% | General Chemical Corp |
| Potassium Carbonate | 6.00% | Armand Products |
| Tetrasodium ethylenediaminetetraacetate | 13.0% | Dow Chemical |
| Water | 62.7% | Deionized |

The solution is added to the system to provide hydrogen peroxide concentrations between about 50 ppb and about 10,000 ppm and quaternary ammonium concentrations to between about 50 ppb and about 10,000 ppm.

Example 4

A concentrated solution is prepared with the following ingredients and concentrations. The mixture may also be diluted with a solvent prior to use, if needed.

| Component | Wt Percent | Source |
| --- | --- | --- |
| n-alkyl dimethyl ethylbenzyl ammonium chloride/n-akyldimethylbenzyl ammonium chloride mixture | 6.00% | Barquat 4250Z (Lonza, Inc.) |
| Hydrogen Peroxide | 6.30% | Solvay |
| Water | 87.7% | Deionized |

The solution is added to the system to provide hydrogen peroxide concentrations between about 50 ppb and about 10,000 ppm and quaternary ammonium concentrations to between about 50 ppb and about 10,000 ppm.

Example 5

A powdered material that may optionally be dissolved in the appropriate solvent (e.g. water) is prepared with the following ingredients and concentrations. The powders can be blended in any number of devices that result in the uniform blending of powders. One such device is a V-blender. The blender should be constructed of appropriate materials.

| Component | Wt Percent | Source |
| --- | --- | --- |
| Soda Ash | 50% | General Chemical Corp |
| Tetrasodium ethylenediaminetetraacetate | 5% | Dow Chemical |

-continued

| Component | Wt Percent | Source |
|---|---|---|
| n-alkyl dimethyl ethylbenzyl ammonium chloride/n-akyldimethylbenzyl ammonium chloride mixture | 10% | Lonza |
| Sodium Percarbonate | 35% | Solvay |

The powder is added to an appropriate amount of water to provide at use hydrogen peroxide concentrations between about 50 ppb and about 10,000 ppm and quaternary ammonium concentrations to between approximately about 50 ppb and about 10,000 ppm.

Example 6

Assays. To investigate the interaction between a commonly used anionic copolymer and the composition of the invention, one determines quantitatively the calcium orthophosphate scale inhibition properties of the copolymer and compares with the results in the presence of the composition of the invention. The study includes a control and calculates the minimum amount of anionic dispersant needed for complete inhibition of calcium orthophosphate.

The composition is then added to the minimum amount of dispersant and observed to see if there is any loss in calcium orthophosphate inhibition. The interaction between the dispersant and the composition of the invention may result in a limited loss in calcium orthophosphate inhibition. An artisan skilled in the art could easily choose specific study parameters such as: 200 mg/L of calcium (as the ion), 9 mg/L orthophosphate, at 60° C. (140° F.), pH 8.5, 24 hour duration.

Biocidal activity of the proposed composition is evaluated utilizing a variety of common microbiological testing mechanisms such as dip slides, biofilm monitoring devices, coupons, and visual inspection of fouling.

All references, including publications, patent applications, patents, and website content cited herein are hereby incorporated by reference to the same extent as if each reference were individually and specifically indicated to be incorporated by reference and was set forth in its entirety herein.

The use of the terms "a" and "an" and "the" and similar referents in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

The word "about," when accompanying a numerical value, is to be construed as indicating a deviation of up to and inclusive of 10% from the stated numerical value. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Unless clearly indicated otherwise, the listing of a company source or a trade name or mark in conjunction with a chemical is only illustrative and does not indicate that the respective chemical must be supplied from the indicated source.

What is being claimed:

1. A method for treating microbial growth in an industrial water system containing an anionic anti-scale or an anionic anti-corrosive agent, or both an anionic anti-scale and anionic anti-corrosive agent comprising:
    adding a composition to a body of water in an industrial water system, the body of water comprising an anionic anti-scaling or anionic anti-corrosive agent or both an anionic anti-scaling and anti-corrosive agent and the composition comprising:
    a peroxide source, which provides a peroxide,
    a phase transfer agent comprising at least one from among a positively charged quaternary ammonium compound, a positively charged phosphonium salt, and a positively charged sulfonium salt, and
    optionally, adding an alkaline compound to the composition or body of water to raise the pH of the body of water to a pH value of greater than 7.0,
    wherein the composition interferes less with the anionic anti-scaling, anionic anti-corrosive agent, or both the anionic anti-scaling and anionic anti-corrosive agents than a composition without an peroxide source and the composition has antimicrobial or biocidal activity.

2. The method of claim 1, wherein the peroxide source comprises a per salt, a hydrogen peroxide, or an organic peroxide.

3. The method of claim 1, wherein the peroxide is between about 50 ppb and 10,000 ppm within the body of water.

4. The method of claim 1, wherein the positively charged phase transfer agent is at least one quaternary ammonium compound.

5. The method of claim 1, wherein the quaternary ammonium compound, positively charged phosphonium salt, or positively charged sulfonium salt is at about 50 ppb and 10,000 ppm within the body of water.

6. The method of claim 1, wherein the quaternary ammonium compound is an alkyl dimethyl benzyl ammonium chloride, an alkyl dimethyl ethylbenzyl ammonium chloride, a dialkyl dimethyl quaternary compound, or a mixture thereof.

7. The method of claim 1, wherein the anionic anti-scaling or anionic anti-corrosive agent is at least one from among acrylates, polyacrylates, acrylic acid terpolymers, acrylamido methyl propyl sulfonic acid, and (2-phosphonobutane-1,2,4-tricarboxylic acid).

8. The method of claim 1, wherein the composition either includes the alkaline compound or the alkaline compound is added to the body of water separately of the composition, either at the time of the addition of the composition or before the addition of the composition.

9. The method of claim 1, wherein the composition further includes at least one from among a surfactant, a dye, a gelling agent and a peroxide activator.

10. The method of claim 1, wherein the composition is prepared as a mixture, or is prepared and transported to the site of end-use as separate compounds or partial mixtures of the compounds therein.

11. The method of claim 10, wherein the mixtures or compounds of the composition are prepared and transported to the site of end-use as powder(s), liquid(s), pellets or tablet(s), or combinations of these forms.

12. The method of claim 1, wherein the composition or compounds thereof are diluted in solvent to prepare concentrated solutions of the composition or the compounds thereof, prior to their addition to the body of water in the industrial water system.

13. The method of claim 12, wherein the peroxide is at a concentration of between about 0.5% and about 90% in the concentrated solution.

14. The method of claim 12, wherein the peroxide is at a concentration of between about 1% and about 50% in the concentrated solution.

15. The method of claim 12, wherein the quaternary ammonium compound, positively charged phosphonium salt, or positively charged sulfonium salt is at a concentration of between about 0.5% and about 90% in the concentrated solution.

16. The method of claim 1, wherein, at use, the concentration of the quaternary ammonium, positively charged phosphonium salt, or positively charged sulfonium salt compound is between about 50 ppb and about 100,000 ppm.

17. The method of claim 1, wherein, at use, the concentration of the peroxide is between about 50 ppb and about 100,000 ppm.

18. The method of claim 17, wherein the concentration of the peroxide is between about 3 ppm and about 10,000 ppm.

19. The method of claim 1, wherein the phosphonium salt is t-butyl phosphonium.

20. The method of claim 1, wherein the sulfonium salt is tributyl sulfonium chloride.

* * * * *